US00PP14562P29

(12) United States Plant Patent
de Jong

(10) Patent No.: US PP14,562 P2
(45) Date of Patent: Feb. 24, 2004

(54) HYPERICUM PLANT NAMED 'KOLMFIR'

(50) Latin Name: *Hypericum inodorum*
Varietal Denomination: Kolmfir

(75) Inventor: Jan de Jong, Heelsum (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/421,313

(22) Filed: Apr. 23, 2003

(51) Int. Cl.[7] ..... A01H 5/00
(52) U.S. Cl. ..... Plt./226
(58) Field of Search ..... Plt./226

(56) References Cited

U.S. PATENT DOCUMENTS

PP10,979 P * 6/1999 van den Bosch ..... Plt./226
PP10,993 P * 7/1999 van den Bosch ..... Plt./226
PP10,994 P * 7/1999 van den Bosch ..... Plt./226
PP11,619 P * 11/2000 van den Bosch ..... Plt./226
PP12,675 P2 * 6/2002 van den Bosch ..... Plt./226
PP13,488 P2 * 1/2003 de Jong ..... Plt./226
PP13,538 P2 * 2/2003 de Jong ..... Plt./226
PP13,540 P2 * 2/2003 de Jong ..... Plt./226
PP13,554 P2 * 2/2003 de Jong ..... Plt./226
PP13,558 P2 * 2/2003 Kolster ..... Plt./226

OTHER PUBLICATIONS

UPOV ROM GTITM Computer Database, GTI Jouve Retrieval Software 2003/04 Citations for 'Kolmfir'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Hypericum plant named 'Kolmfir', characterized by its upright and outwardly spreading plant habit; dark green leaves; bright red-colored fruits; and good postproduction longevity.

2 Drawing Sheets

Botanical classification/cultivar designation: *Hypericum inodorum* cultivar Kolmfir.

BACKGROUND OF THE INVENTION

The present Invention relates to a new and distinct cultivar of Hypericum plant, botanically known as *Hypericum inodorum*, commercially used as cut stems with fruits, and hereinafter referred to by the name 'Kolmfir'.

The new Hypericum is a product of a planned breeding program conducted by the Inventor in Wageningen, The Netherlands. The objective of the breeding program was to develop cut Hypericum varieties with attractive fruit coloration.

The new cultivar originated from a cross made by the Inventor in 1999 of two unidentified proprietary seedling selections, not patented. The cultivar Kolmfir was discovered and selected by the Inventor in 2000 as a flowering plant within the progeny of the stated cross in a controlled environment in Wageningen, The Netherlands.

Asexual reproduction of the new Hypericum by terminal cuttings. taken at Boskoop, The Netherlands, has shown that the unique features of this new Hypericum are stable and reproduced true to type in successive generations of asexual reproduction.

SUMMARY OF THE INVENTION

The following traits have been repeatedly observed and are determined to be the unique characteristics of 'Kolmfir'. These characteristics in combination distinguish 'Kolmfir' as a new and distinct cultivar:

1. Upright and outwardly spreading plant habit.
2. Dark green leaves.

3. Bright red-colored fruits.
4. Good postproduction longevity.

Plants of the new Hypericum differ from plants of the parent seedling selections primarily in fruit coloration.

Plants of the new Hypericum can be compared to plants of the Hypericum cultivar Kolmred, disclosed in U.S. Plant Pat. No. 13,544. In side-by-side comparisons conducted in Boskoop, The Netherlands, plants of the new Hypericum had darker colored fruits than plants of the cultivar Kolmred.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph at the top of the first sheet comprises a side perspective view of a typical plant of 'Kolmfir'.

The photograph at the bottom of the first sheet is a close-up view of typical flowers and a developing fruit of 'Kolmfir'.

The photograph at the top of the second sheet is a close-up view of typical developed fruits of 'Kolmfir'.

The photograph at the bottom of the second sheet is a close-up view of typical stems and leaves of 'Kolmfir'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about two years old. The photographs and description were taken during the summer when outdoor day temperatures ranged from 14 to 30° C. and day temperatures ranged from 7 to 14° C. In the following description, color references are made to The Royal Horticultural Society Colour Chart, 2001 Edition, except where general terms of ordinary dictionary significance are used.

Botanical classification: *Hypericum inodorum* cultivar Kolmfir.

Parentage:

*Female parent.*—Unidentified proprietary selection of *Hypericum inodorum*, not patented.

*Male parent.*—Unidentified proprietary selection of *Hypericum inodorum*, not patented.

Propagation:

*Type.*—Terminal cuttings.

*Time to produce a rooted cutting.*—About 30 days at 20° C.

*Root description.*—Freely branching; medium thickness; brownish green in color.

Plant description:

*Plant form.*—Upright and outwardly spreading perennial woody shrub; globular.

*Growth habit.*—Moderately vigorous. Freely basal branching; dense and bushy growth habit.

*Plant height.*—About 65 cm.

*Plant width (spread).*—About 75 cm.

*Quantity of stems per year.*—About 15.

*Lateral branches.*—Length: About 12.5 cm. Diameter: About 2 mm. Internode length: About 3.2 cm. Strength: Moderate. Texture: Smooth; glabrous. Color, upper surface: 183A to 183B. Color, lower surface: 143B to 143C.

*Foliage description.*—Leaves opposite; single; sessile and generally symmetrical. Length: About 5.3 cm. Width: About 3.2 cm. Shape: Ovate. Apex: Obtuse to acute. Base: Obtuse. Margin: Entire. Texture: Glabrous; slightly rugose. Venation pattern: Pinnate. Color: Developing leaves, upper surface: Between 143A and 144A. Developing leaves, lower surface: Between 138B and 143C. Fully expanded leaves, upper surface: 139A. Fully expanded leaves, lower surface: 138B. Venation, upper and lower surfaces: 144C.

Flower description:

*Flower type and habit.*—Bright yellow single flowers arranged in terminal compound umbels with about seven flowers per umbel. Flowers not fragrant. Flowers not persistent. Flowers upright.

*Natural flowering season.*—Summer, typically July and August in Boskoop, The Netherlands; flowering period typically lasts about 60 days.

*Postproduction longevity.*—Cut flower are typically harvested when all flowers have developed fruits. Postproduction longevity of cut stems with fruits is about two weeks.

*Inflorescence height.*—About 2.8 cm.

*Inflorescence diameter.*—About 4.6 cm.

*Flower buds.*—Height: About 7 mm. Diameter: About 1 cm. Shape: Ovoid. Color: 12A; towards apex, 22A.

*Flowers.*—Diameter: About 2.5 cm. Depth: About 2 cm.

*Petals.*—Quantity per flower: Five. Length: About 1.3 cm. Width: About 7.5 mm. Shape: Obovate. Aspect: Concave. Apex: Obtuse to acute. Base: Attenuate. Margin: Entire. Texture, upper and lower surfaces: Smooth; glabrous. Color: Developing and fully expanded petals, upper surface: 12A; color does not fade with subsequent development. Developing and fully expanded petals, lower surface: 12B; towards the margin and apex, 12A to 13B.

*Sepals.*—Quantity per flower: Five. Length: About 7 mm. Width: About 5 mm. Shape: Ovate. Aspect: Reflexed. Apex: Obtuse. Base: Broadly cuneate. Margin: Entire. Texture, upper and lower surfaces: Smooth; glabrous. Color: Developing sepals, upper and lower surfaces: 183A. Fully expanded sepals, upper surface: 143B to 143C; towards the base, tinged with 183C. Fully expanded sepals, lower surface: 143B; towards the base, tinged with 183C.

*Peduncles.*—Length: About 1.2 cm. Diameter: About 1 mm. Orientation: Erect to about 60° from vertical. Strength: Moderately strong. Color: 178A to 178B.

*Pedicels.*—Length: About 8 mm. Diameter: About 1 mm. Orientation: Erect to about 60° from vertical. Strength: Moderately strong. Color: 143B; overlain with 178B to 178C.

*Reproductive organs.*—Stamens: Quantity per flower: About 85. Stamen length: About 1.1 cm. Filament color: 13A. Anther shape: Broadly ovate. Anther length: About 0.5 mm. Anther color: 14C. Pollen amount: Moderate. Pollen color: 13A to 13B. Pistils: Quantity per flower: Three. Pistil length: About 5 mm. Stigma shape: Globular. Stigma color: Close to 178B to 178C. Style length: About 4.6 mm. Style color: 150C. Ovary color: 8C.

*Fruits.*—Quantity per flower: One. Days to ripening: About 25. Longevity on the plant: About 30 days. Type: Capsule. Shape: Ellipsoidal. Length: About 1.3 cm. Diameter: About 8.5 mm. Texture: Smooth; glabrous. Color: 46B; towards the base, 47B to 47C.

*Seeds.*—Quantity per fruit: More than 100. Length: About 0.8 mm. Diameter: About 0.5 mm. Texture: Smooth; glabrous. Color: 199A to N199A.

Disease/pest resistance: Plants of the new Hypericum have not been observed to be resistant to pathogens and pests common to Hypericum.

Temperature tolerance: Plants of the new Hypericum have been observed to tolerate temperatures ranging from −15 to 35° C.

It is claimed:

1. A new and distinct cultivar of Hypericum plant named 'Kolmfir', as illustrated and described.

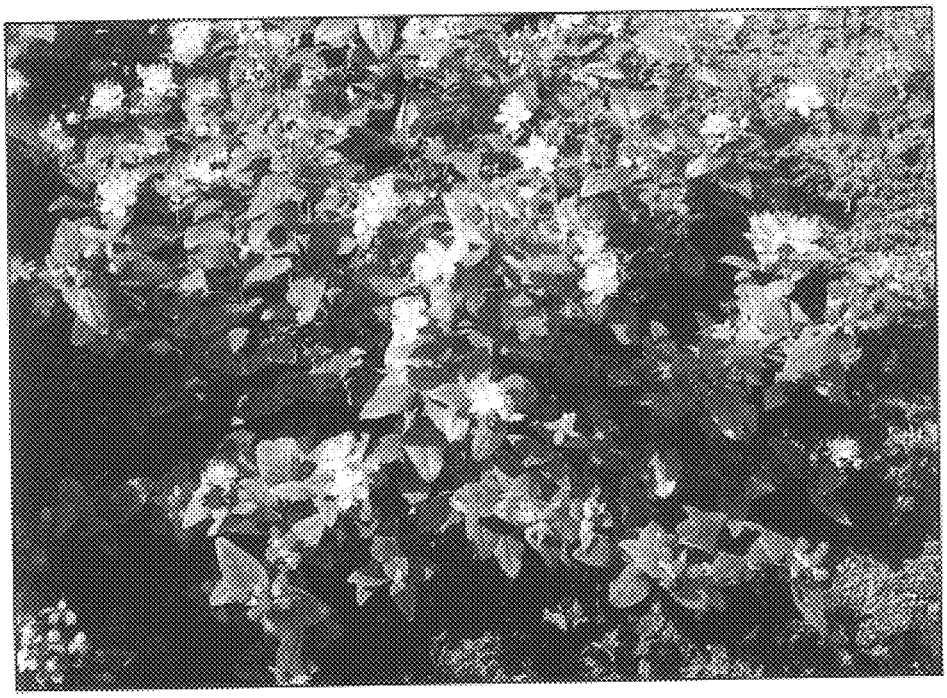
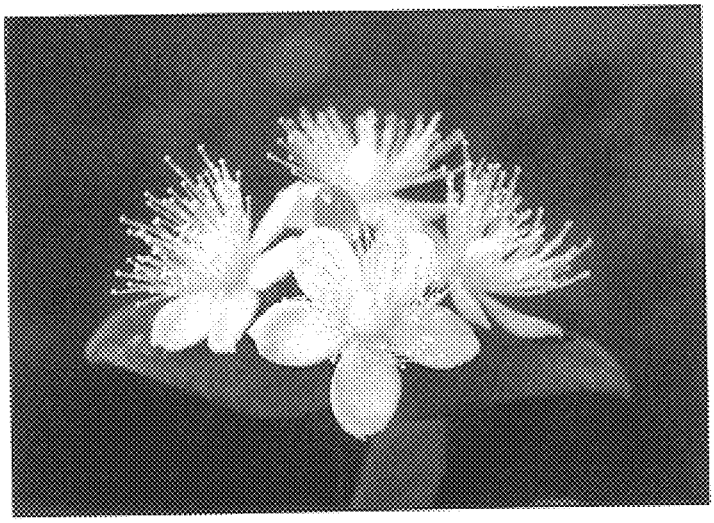

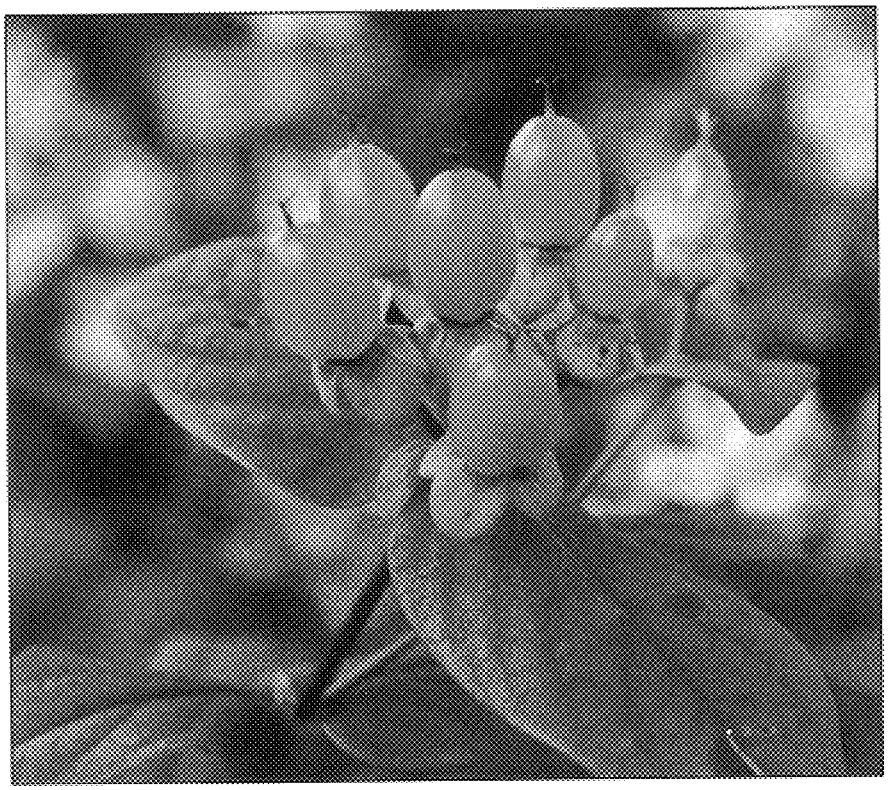
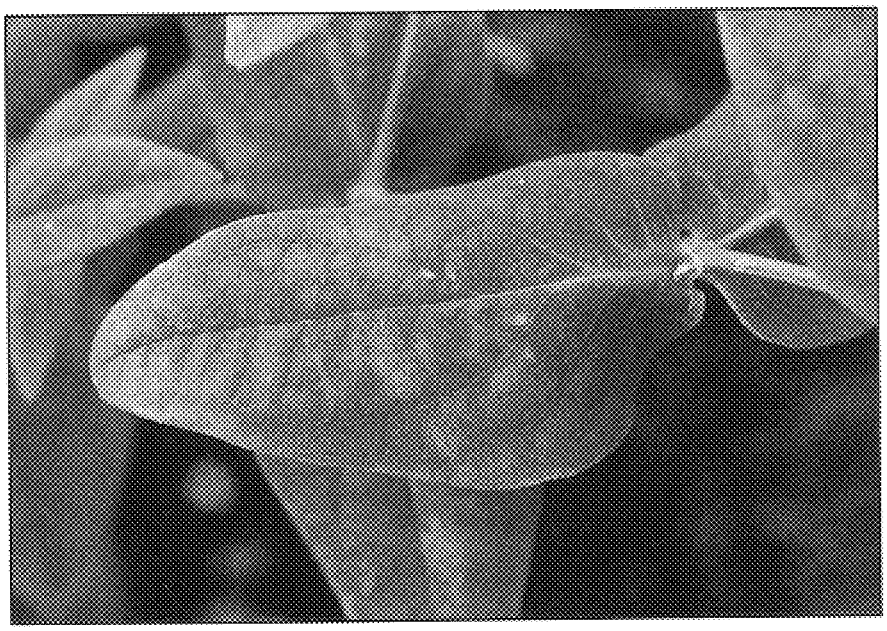

* * * * *